United States Patent [19]
Sheth et al.

[11] Patent Number: 5,482,683
[45] Date of Patent: Jan. 9, 1996

[54] SYSTEM FOR DETECTING THE PRESENCE OF LIQUID IN A VAPOR PHASE STERILIZATION SYSTEM

[75] Inventors: Vipul B. Sheth, Cary; Donald C. Upchurch, Apex, both of N.C.

[73] Assignee: American Sterilizer Company, Erie, Pa.

[21] Appl. No.: 207,912

[22] Filed: Mar. 8, 1994

Related U.S. Application Data

[62] Division of Ser. No. 850,941, Mar. 13, 1992, Pat. No. 5,317,896.

[51] Int. Cl.$^6$ .............................. A61L 2/00; G01N 31/00
[52] U.S. Cl. ........................... 422/119; 422/108; 422/295
[58] Field of Search .............................. 422/28, 105, 108, 422/119, 295, 297, 300

[56] References Cited

U.S. PATENT DOCUMENTS

| | | | |
|---|---|---|---|
| Re. 33,007 | 8/1989 | Bier | 422/28 |
| 1,825,896 | 10/1931 | Bond | 436/147 |

(List continued on next page.)

FOREIGN PATENT DOCUMENTS

| | | |
|---|---|---|
| 0044818 | 1/1982 | European Pat. Off. . |
| 0302420A2 | 2/1989 | European Pat. Off. . |
| 3334999A | 4/1985 | Germany . |
| 3334999C | 10/1986 | Germany . |
| 4102055A1 | 8/1991 | Germany . |

(List continued on next page.)

OTHER PUBLICATIONS

J. HIggins, "Method for measuring the moisture content of air", *Journal of Scientific Instruments*, vol. 36, Jul. 1959.
B. Lainer, *Humidity Sensors*, Sensors, (1986).
Steris System 1™ Processor-Operator Manual, 1988 by Steris Corporation.
Instrumental in Your Practice (description of Statim cassette, date unknown, but prior to Apr. 23, 1991).
VHP™ Technology, A Collection of Scientific Papers, First Edition Jan. 1, 1992, published by Amsco Scientific.
Panametrics, M–Series Probe Brochure, 1984.
General Eastern, 800–Series Polymer Type Relative Humidity Sensor Brochure, 1985.
Panametrics, Hygrometer Brochure, 1986.
EG&G Environmental Equipment, Model 911 Dew–All Bulletin, 1986.
EG&G Environmental Equipment Dew Trak Portable Humidity Meter Bulletim, 1987.
Panametrics, RH Series Hygrometers Brochure, 1987.

*Primary Examiner*—Robert J. Warden
*Assistant Examiner*—Theresa T. Snider
*Attorney, Agent, or Firm*—Jones, Day, Reavis & Pogue

[57] ABSTRACT

A method is provided for detecting moisture in a sterilization chamber or other enclosure (including moisture present on the external or lumened surfaces of an instrument or other load placed in the enclosure). The method includes the steps of exhausting air from the enclosure under vacuum until the pressure in the enclosure is reduced from a starting pressure to a predetermined subatmospheric pressure which is above the saturation pressure of water, and then a second predetermined subatmospheric pressure which is below the saturation pressure of water or other liquid. The times taken to reach each pressure from the starting pressure are measured and their difference is calculated and compared to a reference time difference pre-established for a dry system (or, alternatively, in a known, leak-free system, only the pull-down time period to reach the second subatmospheric pressure is measured and compared to a pre-recorded reference pull-down time for a dry system). When the enclosure contains a lumened instrument, such as an endoscope, fluidly coupled to the exhaust port of the enclosure, the method preferably includes the steps of sensing the temperature in an exhaust conduit fluidly coupled to the exhaust port, during a time period in which the enclosure is evacuated, measuring the minimum temperature reached during the time period and comparing it to a reference minimum temperature pre-established for a dry system.

24 Claims, 2 Drawing Sheets

U.S. PATENT DOCUMENTS

| | | | |
|---|---|---|---|
| 2,836,057 | 5/1958 | Johnson et al. | 73/29.03 |
| 3,561,918 | 2/1971 | Ray | 422/300 |
| 3,886,797 | 6/1975 | Bauer | 73/29.02 |
| 4,064,886 | 12/1977 | Heckele | 134/95 |
| 4,169,123 | 9/1979 | Moore et al. | 422/29 |
| 4,169,124 | 9/1979 | Forstrom et al. | 422/33 |
| 4,230,663 | 10/1980 | Forstrom et al. | 422/33 |
| 4,261,950 | 4/1981 | Bainbridge et al. | 422/26 |
| 4,278,101 | 7/1981 | Tanaka et al. | 134/171 |
| 4,281,674 | 8/1981 | Tanaka et al. | 134/95 |
| 4,282,179 | 8/1981 | Gunther | 422/27 |
| 4,299,244 | 11/1981 | Hirai | 134/102 |
| 4,337,223 | 7/1982 | Kaye | 422/112 |
| 4,380,530 | 4/1983 | Kaye | 422/300 |
| 4,410,492 | 10/1983 | Kaye | 422/27 |
| 4,449,518 | 5/1984 | Konomura et al. | 128/4 |
| 4,489,741 | 12/1984 | Ogasawara | 134/179 |
| 4,491,519 | 1/1985 | Sestak et al. | 141/22 |
| 4,497,773 | 2/1985 | Kuelzow et al. | 422/297 |
| 4,525,220 | 6/1985 | Sasa et al. | 134/21 |
| 4,526,622 | 7/1985 | Takamura et al. | 134/21 |
| 4,526,623 | 7/1985 | Ishii et al. | 134/21 |
| 4,537,209 | 8/1985 | Sasa | 128/4 |
| 4,579,597 | 4/1986 | Sasa et al. | 422/33 |
| 4,579,598 | 4/1986 | Sasa et al. | 422/33 |
| 4,616,501 | 10/1986 | Mechlenburg | 73/24.01 |
| 4,642,165 | 2/1987 | Bier | 422/27 |
| 4,648,978 | 3/1987 | Makinen et al. | 422/28 |
| 4,730,479 | 3/1988 | Pyke et al. | 73/23.21 |
| 4,730,729 | 3/1988 | Mönch | 422/300 |
| 4,731,222 | 3/1988 | Kralovic et al. | 422/37 |
| 4,732,187 | 3/1988 | Mönch | 422/397 |
| 4,744,951 | 5/1988 | Cummings et al. | 422/28 |
| 4,748,007 | 5/1988 | Gaudion et al. | 422/300 |
| 4,763,678 | 8/1988 | Ott | 422/300 |
| 4,843,867 | 7/1989 | Cummings | 422/111 |
| 4,844,052 | 7/1989 | Iwakoshi et al. | 120/4 |
| 4,862,872 | 9/1989 | Yabe et al. | 128/6 |
| 4,863,688 | 9/1989 | Schmidt et al. | 422/28 |
| 4,892,706 | 1/1990 | Kravolic et al. | 422/28 |
| 4,909,999 | 3/1990 | Cummings et al. | 422/298 |
| 4,935,371 | 6/1990 | Rickloff | 435/296 |
| 4,943,414 | 7/1990 | Jacobs et al. | 422/28 |
| 4,952,370 | 8/1990 | Cummings et al. | 422/28 |
| 4,956,145 | 9/1990 | Cummings et al. | 422/28 |
| 4,973,449 | 11/1990 | Kolstad et al. | 422/27 |
| 5,068,087 | 11/1991 | Childers | 422/26 |

FOREIGN PATENT DOCUMENTS

| | | | |
|---|---|---|---|
| 3-68331 | 3/1991 | Japan . | |
| 3-82436 | 4/1991 | Japan . | |
| 3-94759 | 4/1991 | Japan . | |
| 3-123531 | 5/1991 | Japan . | |
| 3-111026 | 5/1991 | Japan . | |
| 3-106332 | 5/1991 | Japan . | |
| 3-151931 | 6/1991 | Japan . | |
| 3-176022 | 7/1991 | Japan . | |
| 3-176061 | 7/1991 | Japan . | |
| 3-215242 | 9/1991 | Japan . | |
| 2-10505 | 9/1991 | Japan . | |
| 3-221027 | 9/1991 | Japan . | |
| 3-295535 | 12/1991 | Japan . | |
| 785707 | 12/1980 | U.S.S.R. . | |
| 1519701A | 11/1989 | U.S.S.R. . | |
| 0921887 | 3/1963 | United Kingdom | 73/29.02 |
| 1275833 | 5/1972 | United Kingdom . | |
| 1582060 | 12/1980 | United Kingdom . | |
| 2052800 | 1/1981 | United Kingdom . | |
| 2097130 | 10/1982 | United Kingdom | 73/29.02 |
| 2105591 | 3/1983 | United Kingdom . | |
| 2127692 | 4/1984 | United Kingdom . | |
| 2191585 | 12/1987 | United Kingdom . | |
| WO8906358A | 7/1989 | WIPO . | |
| WO9012312A | 10/1990 | WIPO . | |

SYSTEM FOR DETECTING THE PRESENCE OF LIQUID IN A VAPOR PHASE STERILIZATION SYSTEM

This is a divisional of application Ser. No. 07/850,941, filed on Mar. 13, 1992, now U.S. Pat. No. 5,317,896.

FIELD OF THE INVENTION

The present invention relates generally to liquid detection methods, and more particularly to a method of detecting moisture in a sterilization system that employs a corrosive, vapor phase sterilant.

BACKGROUND OF THE INVENTION

In general, the various lumens of an endoscope that has been used on a patient are first cleaned with brushes that remove gross debris, like fecal matter, and are then flushed with a liquid such as alcohol or water, and dried with pressurized air forced through the lumens. The outside surfaces of the endoscope are then wiped dry with a lint-free cloth.

Occasionally, an instrument may not be thoroughly dried or the drying step may be skipped accidentally altogether. Thus, moisture on the internal or external surfaces of the instrument may be inadvertently introduced into the sterilization system. Water splashed accidentally into the chamber may also increase the level of moisture present when sterilization begins.

It is generally desired to limit the amount of moisture present in a vapor phase sterilization system. Water in the sterilization cheer, or on the internal or external surfaces of a load placed in the chamber, may act as a barrier and prevent sterilant vapor from effectively contacting the surfaces to be sterilized. Also, water may cause condensation of the liquid sterilant, thereby diluting the concentration of sterilant vapor and reducing its efficacy or requiring longer kill times. In addition, condensed sterilant, such as liquid hydrogen peroxide, may degrade or harm the contents of the sterilization chamber. Synthetic materials employed in flexible endoscopes, for example, may be degraded by condensed hydrogen peroxide.

When a sterilant vapor such as hydrogen peroxide, which is a strong oxidizer and corrosive to a wide range of metals, is employed, a conventional humidity detector, which directly senses humidity levels, should not be employed. The corrosive vapors may easily damage or destroy such a humidity detector.

There is a need for a method of accurately detecting moisture levels in a vapor phase sterilization system, to alert the user to remove any excess water (i.e., an amount of water that is unacceptable for the intended application) before sterilization proceeds. There is a further need for an indirect method of detecting moisture in a sterilization system employing a corrosive vapor sterilant.

SUMMARY

The present invention provides a method for detecting moisture in a sterilization chamber or other enclosure (including moisture present on the external or lumened surfaces of an instrument, such as an endoscope, or other load placed in the enclosure). The method succeeds in indirectly detecting the presence of excess moisture, by monitoring pressure changes and/or temperature changes, over measured periods of time during which the enclosure is evacuated, at close to ambient temperature, to a predetermined pressure below the saturation pressure of water.

When the vacuum is applied, and the pressure in the enclosure begins to decrease, water (if present) begins to evaporate. As the pressure in the enclosure continues to decrease, evaporated water is drawn from the enclosure into the vacuum source (due to the negative pressure differential created by the vacuum). As lower pressure levels are reached, water continues evaporating, at increasing rates, to reassert equilibrium. The vapor pressure of the evaporating water renders it increasingly difficult to continue pulling a vacuum down to the predetermined subatmospheric pressure, particularly when the pressure in the enclosure drops below the saturation pressure of water.

In accordance with one embodiment of the invention, a pressure sensor monitors the pressure in the enclosure as it is pulled down under vacuum from a starting pressure to a predetermined subatmospheric pressure (preferably about 20 mm Hg absolute at ambient temperature) below the saturation pressure of water. The time period elapsing during pull-down from the starting pressure to the subatmospheric pressure is measured, and compared with a reference pull-down time period, which has previously been recorded by carrying out the same steps on a reference dry system or other reference system containing a known, acceptable amount of moisture. If excess moisture is present, the measured pull-down time period will be longer than the reference pull-down time period.

In another embodiment of the invention, which is used when a leak-proof vacuum has not been ensured, the time period elapsing during pull-down from the starting pressure to a predetermined subatmospheric pressure above the saturation pressure of water, preferably about 30 mm Hg absolute at ambient temperature, is also measured. The difference between the measured pull-down time periods is calculated, and compared to a reference time difference which has previously been recorded by carrying out the same steps on a reference dry system or other reference system containing a known acceptable amount of moisture. If the system is dry or contains an acceptable amount of moisture, the time taken to pull down to the first pressure from atmospheric pressure will be close to the time taken to pull down from atmospheric pressure to the second pressure. But if excess moisture is present, the vacuum will start to stall at about the saturation pressure of water or other liquid, and it will take much longer to pull down to the second pressure. Thus, if excess moisture is present, the time difference calculated for the measured system will be greater than the reference time difference calculated for the reference system.

In another embodiment of the invention (preferably practiced when the enclosure contains a lumened instrument, such as an endoscope fluidly coupled to an exhaust port of the enclosure, which in turn is fluidly coupled to the vacuum source), the method comprises the separate or additional steps of sensing the temperature in an exhaust conduit fluidly coupled to the exhaust port, during a period of time in which the enclosure is evacuated. Water droplets, if present in the lumens of the instrument, will be drawn off by the vacuum, along with air and water vapor, directly over the temperature sensor. The exhausted water droplets will impinge and have a cooling effect on the temperature sensor, causing the sensed temperature to drop. The minimum temperature measured during the time period is compared with a reference minimum temperature, previously determined by carrying out the same steps on a reference dry system or another reference system containing a known, acceptable amount of moisture. If excess moisture is present, then, the measured minimum temperature will be lower than the reference minimum temperature.

When the method of the present invention is practiced with a sterilization chamber, the user can be alerted to the presence of moisture in the chamber (including its contents), before the sterilization cycle begins. Thus, the chamber and/or its contents can be removed and dried, before sterilization proceeds, to ensure that efficacious and quick sterilization can then be achieved, without undue condensation of sterilant.

It is contemplated that the steps of the method of the present invention can be conducted to detect the presence of other liquid contaminants besides water, such as alcohol. In that case, the method is carried out in the same manner as herein described for detecting moisture, except that the reference pull down time periods/pull down time differences/temperature differences are determined for either a dry reference system or a reference system containing a known, acceptable amount of the liquid contaminant. Also, the saturation pressure of the other liquid is substituted for the saturation pressure of water.

BRIEF DESCRIPTION OF THE DRAWING

The present invention may be better understood by reference to the drawing, in which.

DETAILED DESCRIPTION OF THE INVENTION

The present invention can be used to detect moisture in an enclosure (including its contents, if any) where excessive moisture levels should be avoided, such as a sterilization chamber that uses a gaseous sterilant. The invention is particularly suited for detecting moisture both internal and external to a lumened instrument (such as an endoscope), placed in a sterilization chamber, wherein the lumened instrument has at least two open ends and a fluid path there-between, and at one such end is fluidly connected to an exhaust port of the sterilization chamber, which is fluidly connected to a vacuum source.

Figure 1:
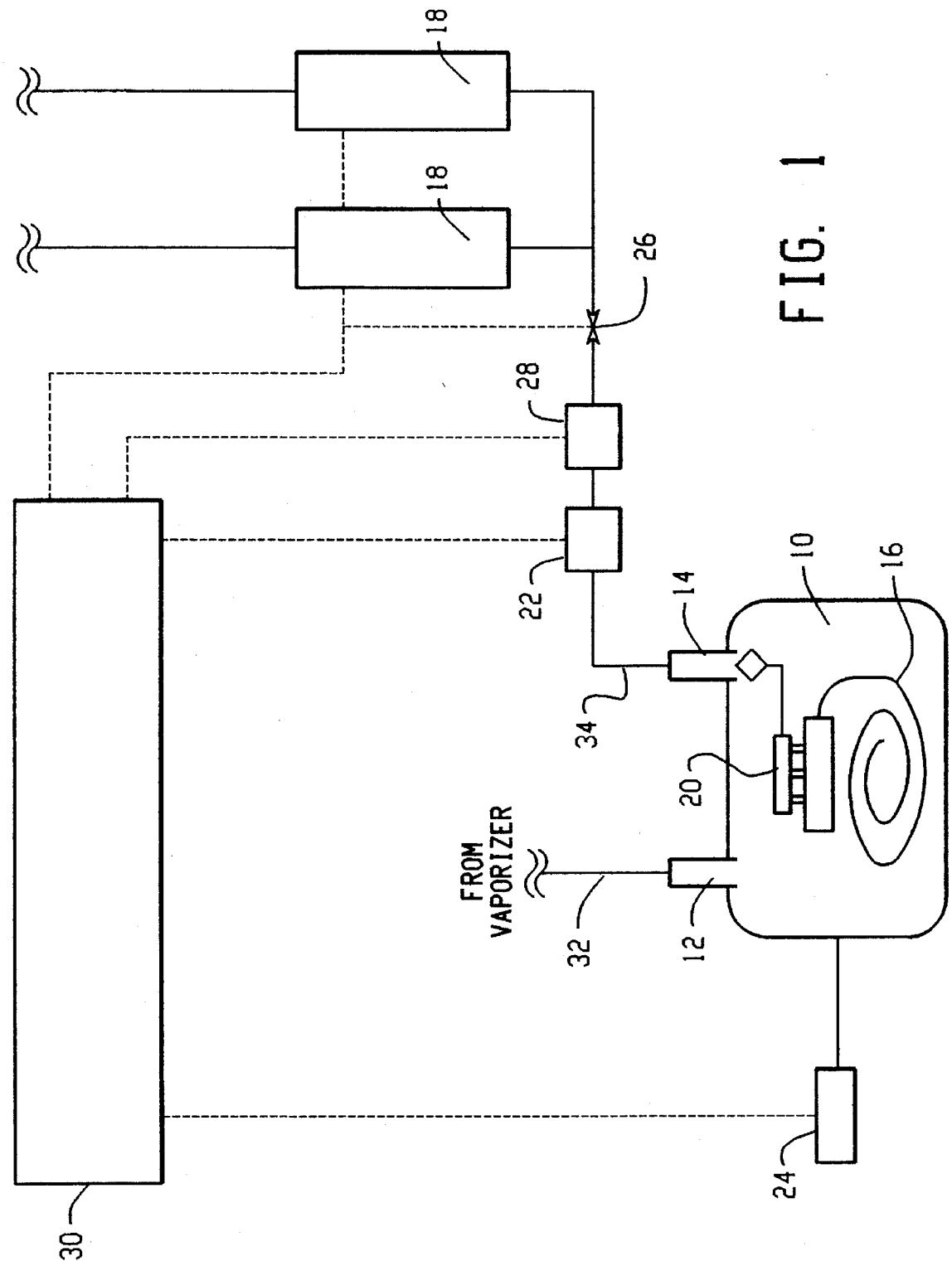
FIG. 1 is a schematic diagram of an exemplary system for practicing the present invention.

FIG. 1 illustrates an exemplary system for detecting moisture in a sterilization chamber containing an endoscope in accordance with an embodiment of the invention. In the illustrated example, the sterilization chamber is a sealable and removeable cassette 10, described in commonly assigned, copending application U.S. Ser. No. 07/851,096, entitled "Device and System for Sterilizing Objects," filed on Mar. 13, 1992, now abandoned in favor of continuation application Ser. No. 08/282,228, filed on Jul. 29, 1994, and incorporated by reference herein.

The cassette 10 includes an inlet port 12, fluidly coupled to inlet conduit 32, for receiving sterilant vapor from the vaporizer and an outlet port 14, fluidly coupled to an exhaust conduit 34, for exhausting gases. The cassette 10 houses a flexible endoscope 16 which is fluidly coupled at one lumened end to the outlet port 14 and exhaust conduit 34, via a connector 20.

A suitable known temperature sensing device 22, such as a thermocouple or resistive temperature device, is positioned in the exhaust conduit 34 near the exhaust port 14, directly in the path of gas exhausted from the cassette as it is evacuated, to monitor the temperature of the exhaust gases.

A suitable pressure sensor 24, such as a pressure transducer, is positioned on the cassette 10, to monitor the pressure in the cassette. It is contemplated that the pressure sensor 24 could also be placed in the exhaust conduit 34 near the exhaust port 14, housed separately or together with temperature sensor 22.

An exhaust valve 26 is positioned in the exhaust line between pumps 18 and thermocouple 22. The pumps are preferably two-stage, oil-free vacuum pumps. The pumps create a negative pressure differential across the cassette 10, when exhaust valve 26 is opened and a valve (not shown) upstream of the vaporizer is closed, and draw air (and moisture, if present) from the cassette 10, directly over the temperature sensor 22, through the exhaust conduit 34. A hydrophobic filter 28 is positioned between the pumps 18 and the thermocouple 22 to prevent water from damaging the pumps.

The illustrated system includes a microprocessor 30 for controlling the steps of the method of the invention, and also the sterilization cycle of the endoscope. While the use of a microprocessor is preferred, it is also contemplated that the present invention can be carried out manually.

Figure 2:
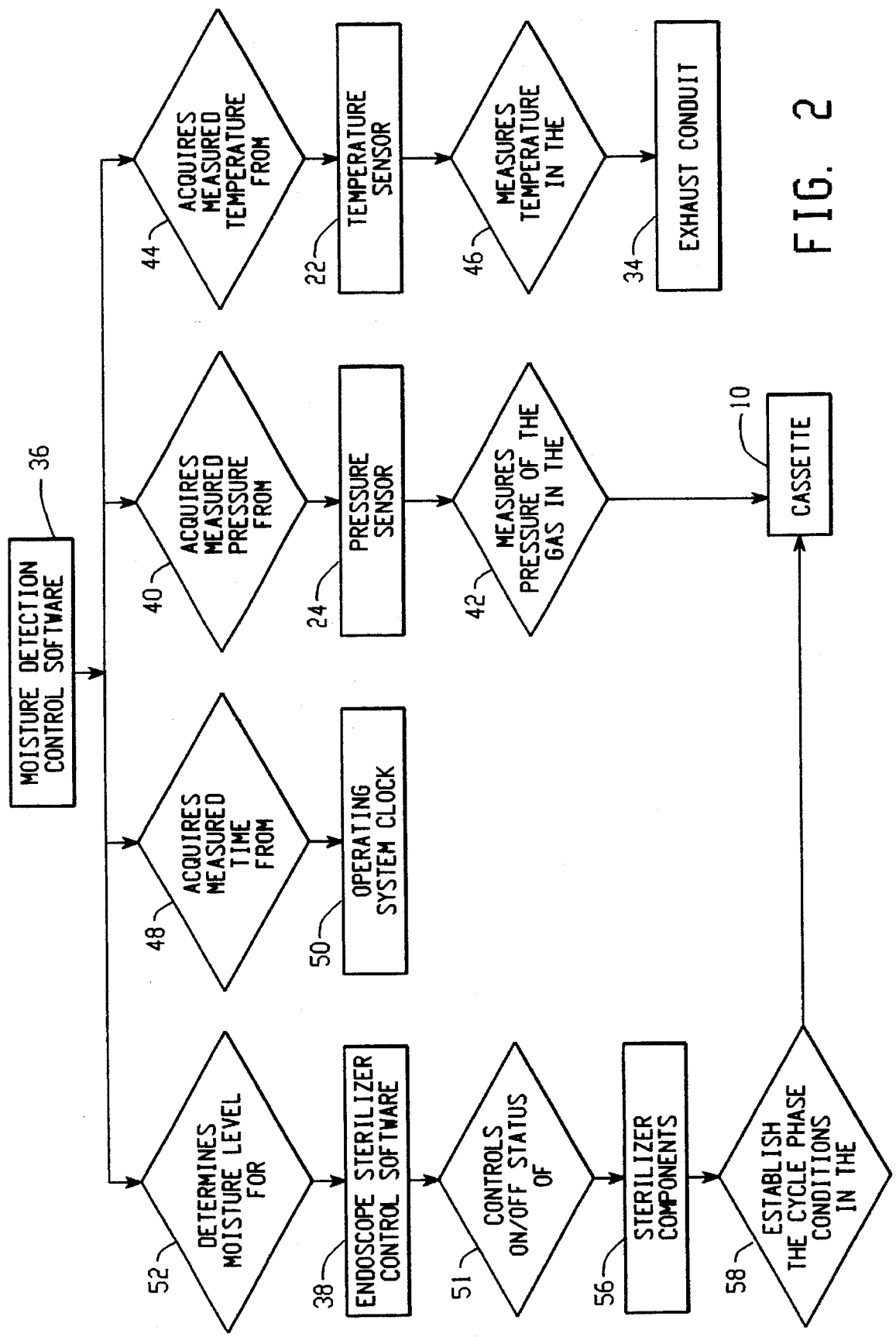
FIG. 2 is an information diagram illustrating the steps carried out in an embodiment of the invention, by components of the exemplary system illustrated in FIG. 1.

The manner in which the presence of moisture in cassette 10 (including the internal and external surfaces of the endoscope 16 and the internal surfaces of the cassette 10) can be detected in accordance with the present invention will now be further described with reference to FIG. 2. In FIG. 2, the microprocessor includes software 36 for controlling the moisture detection method of the present invention and also software 38 for controlling the operation of endoscope sterilizer.

The moisture detection control software 36 receives an input signal through operation 40 from pressure sensor 24 which is representative of the pressure of gas in the cassette 10 measured through operation 42 by the pressure sensor 24 and an input signal 44 from the temperature sensor 22 which is representative of the temperature, measured through operation 46 by the temperature sensor 22, in the exhaust conduit 34. The moisture detection control software also receives an input signal 48 from an operating system clock 50, which is representative of the time elapsing while the steps of the method are carried out.

Under vacuum supplied by pumps 18, the cassette 10 is evacuated to reduce the pressure in the cassette 10, as measured by pressure sensor 24, to a first predetermined subatmospheric pressure above the saturation pressure of water (at 76° F., the saturation pressure of water is 23 mm Hg.) Evacuation is continued until the pressure in the cassette 10 is reduced to a second subatmospheric pressure below the saturation pressure of water. When the method is carried out at about room temperature, to detect moisture, the predetermined subatmospheric pressures above and below the saturation pressure of water are preferably 30 mm Hg and 20 mm Hg, respectively.

If water is present in the system (either on the internal or external surfaces of the endoscope or otherwise inside the cassette), such water will begin evaporating when the vacuum is applied. As lower pressures are reached, the rate of evaporation increases and the vapor pressure of the water vapor renders it increasingly difficult to continue pulling down to lower pressures, particularly when the pressure in the enclosure drops below the saturation pressure of water or other liquid.

To determine the presence of moisture in the cassette (including the internal and external surfaces of the endoscope), the pull-down time periods to the first and second subatmospheric pressures from the starting pressure are measured, and their difference is calculated. In the presence of excess water, the difference between the pull-down time periods to the first and second pressures will be much longer than the difference between reference time periods pre-established by carrying out the same steps on a dry reference system or other reference system containing a known acceptable amount of moisture. (Alternatively, the measured pull-down time period to the second pressure may simply be compared to a corresponding reference pull-down time period. In the absence of interfering air leaks, the measured pull-down time period to the second pressure will be longer than the corresponding reference pull-down time period, if excess moisture is present).

If it is desired to determine the amounts of moisture present, reference tests can be conducted by carrying out the steps of the present invention with a dry system and selected systems containing known added amounts of moisture. Reference time periods can be established which provide standards for determining if the cassette 10 and/or endoscope 16 contain unacceptable moisture levels for a particular application. The reference time periods can be programmed into the microprocessor or otherwise pre-recorded.

In FIG. 2, the moisture detection control software 36 has been programmed with reference pull-down time periods (and their difference), predetermined for a dry system or other reference system containing an unacceptable amount of moisture. The moisture detection control software determines at operation 52 if excess moisture is present, by comparing the calculated difference between the measured pull-down time periods with the difference in pull-down times calculated for the reference system. If the difference between the measured pull-down time periods is greater than the difference in the reference pull-down time periods, the user can be alerted by a suitable display to remove and dry the endoscope and cassette before proceeding through the sterilization cycle. Alternatively, as illustrated in FIG. 2, the moisture detection control software 36 can be programmed to instruct the endoscope sterilizer control software 38 through operation 52 that unacceptable moisture is present. The endoscope sterilizer control software 38 controls through operation 54 the on/off status 54 of the components of the sterilizer system 56 which establish the cycle phase conditions 58 in the cassette 10. In the presence of excess moisture, the endoscope sterilizer control software 38 is programmed to instruct the sterilizer system to enter an extended drying phase and to prevent the sterilizer system from entering a sterilization cycle until acceptable moisture levels are detected.

The moisture detection software also preferably senses the minimum temperature reacted in the exhaust conduit 34 during a time period in which the cassette is evacuated. Water droplets, if present in the endoscope lumens, will be carried off with the exhaust gases, and will have a cooling effect on the temperature sensor 22. In the presence of excess water, the measured minimum time difference will be lower than the minimum time difference pre-established from a reference dry system or other reference system containing a known, acceptable amount of moisture.

The actual magnitude of temperature decrease will depend on the amount of water present in the lumens. Where it is desired to determine the amount of moisture present, reference tests can be conducted by carrying out the steps of the invention for systems containing known amounts of water in the lumens. Reference minimum temperatures can then be programmed into the microprocessor 30 or otherwise pre-recorded, for comparison with the measured minimum temperature decrease.

In FIG. 2, the moisture detection control software 36 has been preprogrammed with a reference minimum temperature for a system containing an acceptable amount of water for the intended endoscope application. The moisture detection control software 52 determines if excess moisture is present by comparing the measured minimum temperature achieved during pull down in the specified time with the reference minimum temperature. If the measured minimum temperature is lower than the reference temperature, the user can be alerted, by a suitable display, to remove the endoscope 16 and dry its lumens before the sterilization cycle begins. Alternatively, as illustrated in FIG. 2, the moisture detection control software 36 can be programmed to instruct at operation 52 the endoscope sterilizer control software 38 that unacceptable levels of moisture are present. The endoscope sterilizer control software 38 then instructs the sterilizer system to enter an extended drying phase or prevent the sterilization cycle from commencing, until acceptable moisture levels are detected.

Through the use of the method of the present invention, excess moisture in the cassette 10, including the extended and lumened surfaces of the endoscope 16 can be detected (and then removed) before the sterilization cycle begins. Quick and/or efficacious sterilization is assured, and harmful condensation of sterilant vapor is avoided. Further, the method can effectively detect moisture levels in a sterilization system that employs a corrosive sterilant vapor, such as hydrogen peroxide.

EXAMPLE

A system was set up as illustrated in FIG. 1 to test the method of the present invention with a flexible endoscope 16 fluidly coupled to the cassette exhaust port 14 via the manifold connector 20. In each test run, the cassette was evacuated for a first period of time sufficient to bring the cassette pressure from ambient to a pressure of 30 mm Hg and then for a second period of time sufficient to lower the pressure from ambient to 20 mm Hg. The first and second time periods were measured by a stopwatch and recorded. The minimum temperatures sensed during the pull-down from ambient to 20 mm Hg were also recorded. In one series of test runs, an OLYMPUS CF 10L endoscope was employed; in a second series of test runs, an OLYMPUS GIF-XPIO endoscope was used, the latter endoscope having a relatively narrower and shorter working channel than the former endoscope.

A first test run for each series was conducted using a dry cassette and dry endoscope. The endoscopes were rendered dry by blowing filtered room air at a dynamic pressure of 10 psi through their channels for 45 minutes. The external surfaces of the endoscopes were also wiped dry with a lint free, clean cloth. The cassette was dried by wiping with a lint free cloth.

A second test run for each series was conducted using a dry cassette and a wet endoscope. The wet endoscope was obtained by syringing water through the endoscope channels, and placing the wet endoscope in the cassette without drying (leaving about 3 grams of water, as measured by weighing the dry and wet endoscopes, clinging to the endoscope lumens).

A third test run for each series was conducted using the dried endoscope and a wet cassette. The wet cassette was obtained by spraying about 10 cc of water in the cassette and on the external endoscope surfaces.

The test data obtained for the two series of test runs is reported in Table I:

TABLE I

| ENDOSCOPE TYPE | MOISTURE CONDITIONS | TIME TO 30 MM HG SECONDS | TIME TO 20 MM HG SECONDS | MINIMUM EXHAUST TEMPERATURE °F. |
| --- | --- | --- | --- | --- |
| CF-10L | DRY SCOPE DRY CASSETTE | 50 | 62 | 94 |
| CF-10L | WET SCOPE DRY CASSETTE | 53 | 200 | 60 |
| CF-10L | DRY SCOPE WET CASSETTE | 57 | 90 | 100 |
| GIF-XP10 | DRY SCOPE DRY CASSETTE | 50 | 62 | 77 |
| GIF-XP10 | WET SCOPE DRY CASSETTE | 59 | greater than 180 | 58 |
| GIF-XP10 | DRY SCOPE WET CASSETTE | 54 | greater than 180 | 76 |

The results of the test illustrate that when the cassette 10 and endoscope 16 were both dry (as should be the case where recommended cleaning and drying procedures are carried out prior to sterilization), the time taken to reach 20 mm Hg absolute from ambient pressure was only fractionally higher than the time taken to reach 30 mm Hg absolute from ambient pressure. However, if either the lumens of the endoscope were wet, or there was water in the cassette 10 or on the external endoscope surfaces, the time period to reach 20 mm Hg absolute was much longer than the time taken to reach 30 mm Hg absolute.

The above results illustrate the need to measure pull-down time periods from two pressures, one above the saturation pressure of water (about 23 mm Hg at 76° F.), and one below the saturation pressure of water—as oposed to one pull-down time period for a pressure below the saturation pressure of water—in the presence of system air leaks. As shown in Table I, the time taken to reach 30 mm Hg in each case was about the same. Before the saturation pressure of water is reached, water evaporates at a slower rate than the rate at which water vapor is withdrawn and the pumps can still continue pulling a vacuum. At the saturation pressure of water, water begins to evaporate at the same rate that is being carried away. Therefore, the vacuum pumps begin stalling at the saturation pressure of water, rendering continued pull-down increasingly difficult to achieve. Thus, in the presence of moisture, the measured time taken to pull down to 20 mm Hg is much longer than the time taken to pull-down to 30 mm Hg, in comparison to a reference system. (In the presence of moisture, the measured pull-down time period to 20 mm Hg should also be longer than the corresponding reference time period, provided that the longer measured pull-down time is not caused by air leaks in the measured system.)

The results of the test also clearly indicate that when the lumens of the endoscope 16 were wet, the temperature dropped down to about 60° F., as compared to about 77° F. or above for a dry scope.

While the invention is susceptible to various modifications and alternative forms, the preferred embodiments have been described herein in detail. It is to be understood, however, that it is not intended to limit the invention to the specific forms disclosed. On the contrary, it is intended to cover all modifications and alternative forms falling within the spirit and scope of the invention.

What is claimed is:

1. A system for detecting the presence of liquid, having a saturation pressure, in an enclosure, comprising:

(a) an enclosure having at least one exhaust port;

(b) a vacuum source fluidly coupled to the exhaust port of said enclosure;

(c) a microprocessor programmed to store a first predetermined reference time period, and a predetermined subatmospheric pressure that is below the saturation pressure of the liquid;

(d) a pressure sensing means for sensing the pressure in said enclosure, electrically interconnected to said microprocessor;

(e) said microprocessor further programmed to measure a time period in which the enclosure pressure is reduced from the starting pressure to the stored predetermined subatmospheric pressure;

(f) said microprocessor further programmed to compare the measured time period with the stored predetermined reference time period, wherein a difference between the measured time period and the stored predetermined reference time period provides a detection of the presence of liquid in said enclosure.

2. The system of claim 1, wherein the liquid is water.

3. The system of claim 2, wherein the predetermined pressure is about 20 mm Hg.

4. The system of claim 1, wherein the enclosure is a sterilization chamber.

5. The system of claim 4, wherein the chamber is a cassette.

6. The system of claim 1, further comprising:

(a) an exhaust conduit fluidly coupled to the exhaust port of said enclosure;

(b) said exhaust conduit further fluidly coupled to said vacuum source;

(c) temperature sensing means positioned within said exhaust conduit, electrically interconnected to said microprocessor;

(d) said microprocessor further programmed to store a predetermined reference temperature and a second predetermined reference time period for a reference system;

(e) said microprocessor further programmed to store the minimum measured temperature in the exhaust conduit for the stored second predetermined reference time period while the vacuum source is exhausting air from said enclosure;

(f) said microprocessor further programmed to compare the minimum measured temperature with the stored predetermined reference temperature, wherein a difference between the minimum measured temperature and the stored predetermined reference temperature also provides a detection of the presence of liquid in said enclosure.

7. The system of claim 6, wherein the reference predetermined time period comprises the measured period of time in which the enclosure pressure is reduced from a starting pressure to the predetermined subatmospheric pressure below the saturation pressure of the liquid.

8. The system of claim 7, further comprising an article contained within the enclosure, said article having at least one lumen therein fluidly connected to the exhaust port of the enclosure, the system further providing detection of the presence of liquid in said lumen.

9. A system for detecting the presence of liquid, having a saturation pressure, in an enclosure, comprising:

(a) an enclosure having at least one exhaust port;

(b) a vacuum source fluidly coupled to the exhaust port of said enclosure;

(c) a microprocessor programmed to store a predetermined reference time period, a first predetermined subatmospheric pressure that is above the saturation pressure of the liquid, and a second predetermined subatmospheric pressure that is below the saturation pressure of the liquid;

(d) a pressure sensing means for sensing the pressure in said enclosure, electrically interconnected to said microprocessor;

(e) said microprocessor further programmed to measure a first time period in which the enclosure pressure is reduced from the starting pressure to the first stored predetermined subatmospheric pressure;

(f) said microprocessor further programmed to store the first measured time period;

(g) said microprocessor further programmed to measure a second time period in which the enclosure pressure is reduced from the starting pressure to the second stored predetermined subatmospheric pressure;

(h) said microprocessor further programmed to calculate the difference between the first measured time period and the second measured time period;

(i) said microprocessor further programmed to compare the calculated time difference with the stored predetermined reference time period, wherein a difference between the calculated time difference and the stored predetermined reference time period provides a detection of the presence of liquid in said enclosure.

10. The system of claim 9, wherein the liquid is water.

11. The system of claim 10, wherein the second predetermined pressure is about 20 mm Hg.

12. The system of claim 10, wherein the first predetermined pressure is about 30 mm Hg.

13. The system of claim 9, wherein the enclosure is a sterilization chamber.

14. The system of claim 13, wherein the chamber is a cassette.

15. The system of claim 9, further comprising:

(a) an exhaust conduit fluidly coupled to the exhaust port of said enclosure;

(b) said exhaust conduit further fluidly coupled to said vacuum source;

(c) temperature sensing means positioned within said exhaust conduit, electrically interconnected to said microprocessor;

(d) said microprocessor further programmed to store a predetermined reference temperature and a second predetermined reference time period for a reference system;

(e) said microprocessor further programmed to store the minimum measured temperature in the exhaust conduit for the stored second predetermined reference time period while the vacuum source is exhausting air from said enclosure;

(f) said microprocessor further programmed to compare the minimum measured temperature with the stored predetermined reference temperature, wherein a difference between the minimum measured temperature and the stored predetermined reference temperature also provides a detection of the presence of liquid in said enclosure.

16. The system of claim 15, wherein the predetermined reference time period comprises the measured period of time in which the enclosure pressure is reduced from a starting pressure to the second predetermined pressure below the saturation pressure of the liquid.

17. The system of claim 16, further comprising an article contained within the enclosure, said article having at least one lumen therein fluidly connected to the exhaust port of the enclosure, the system further providing for detection of liquid in said lumen.

18. A system for detecting the presence of liquid, having a saturation pressure, in an enclosure, comprising:

(a) an enclosure having at least one exhaust port;

(b) an exhaust conduit having a first and a second end, the first end being fluidly connected to the exhaust port of said enclosure, and the second end being fluidly connected to a vacuum means for exhausting air from said enclosure through the exhaust port of said enclosure;

(c) a microprocessor programmed to store a predetermined reference temperature and a predetermined reference time period;

(d) a temperature sensor positioned within said exhaust conduit, electrically interconnected to said microprocessor;

(e) said microprocessor further programmed to store the minimum measured temperature in the exhaust conduit for the stored predetermined reference time period while the vacuum means is exhausting air from said enclosure;

(f) said microprocessor further programmed to compare the minimum measured temperature with the stored predetermined reference temperature, wherein a difference between the minimum measured temperature and the stored predetermined reference temperature provides a detection of the presence of liquid in said enclosure.

19. The system of claim 18, wherein the liquid is water.

20. The system of claim 18, wherein the enclosure is a sterilization chamber.

21. The system of claim 20, wherein the chamber is a cassette.

22. The system of claim 20, further comprising an article contained within the chamber, said article having at least one lumen therein fluidly connected to the exhaust port of the enclosure, the system further providing for detection of the presence of liquid in said lumen.

23. The system of claim 18, further comprising:

(a) a pressure sensing means for sensing the pressure in said enclosure, electrically interconnected to said microprocessor;

(b) said microprocessor further programmed to store a second predetermined reference time period and a predetermined subatmospheric pressure that is below the saturation pressure of the liquid;

(c) said microprocessor further programmed to measure a time period in which the enclosure pressure is reduced from the starting pressure to the stored predetermined subatmospheric pressure;

(d) said microprocessor further programmed to compare the measured time period with the second stored predetermined reference time period, wherein a difference between the measured time period and the second stored predetermined reference time period also provides a detection of the presence of liquid in said enclosure.

24. The system of claim 18, further comprising:

(a) a pressure sensing means for sensing the pressure in said enclosure, electrically interconnected to said microprocessor;

(b) said microprocessor further programmed to store a second predetermined reference time period, a first predetermined subatmospheric pressure that is above the saturation pressure of the liquid, and a second predetermined subatmospheric pressure that is below the saturation pressure of the liquid;

(c) said microprocessor further programmed to measure a first time period in which the enclosure pressure is reduced from the starting pressure to the first stored predetermined subatmospheric pressure;

(d) said microprocessor further programmed to store the first measured time period;

(e) said microprocessor further programmed to measure a second time period in which the enclosure pressure is reduced from the starting pressure to the second stored predetermined subatmospheric pressure;

(f) said microprocessor further programmed to calculate the difference between the first measured time period and the second measured time period;

(g) said microprocessor further programmed to compare the calculated time difference with the second stored predetermined reference time period, wherein a difference between the calculated time difference and the second stored predetermined reference time period also provides a detection of the presence of liquid in said enclosure.

* * * * *